: US 7,270,998 B2
(45) Date of Patent: Sep. 18, 2007

(12) United States Patent
Okano et al.

(54) METHOD OF CONCENTRATING AND SEPARATING DOPAMINERGIC NEURONS

(75) Inventors: Hideyuki Okano, Osaka (JP); Kazunobu Sawamoto, Osaka (JP); Kazuto Kobayashi, Fukushima (JP); Natsuki Matsushita, Fukushima (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/048,536

(22) PCT Filed: Dec. 7, 2000

(86) PCT No.: PCT/JP00/08674

§ 371 (c)(1),
(2), (4) Date: Mar. 13, 2002

(87) PCT Pub. No.: WO01/92482

PCT Pub. Date: Dec. 6, 2001

(65) Prior Publication Data

US 2002/0155423 A1 Oct. 24, 2002

(30) Foreign Application Priority Data

Jun. 1, 2000 (JP) .............................. 2000-165150

(51) Int. Cl.
*C12N 5/00* (2006.01)
*C12N 5/02* (2006.01)
*C12Q 1/00* (2006.01)
*G01N 3/00* (2006.01)
*A01K 67/00* (2006.01)
*A01K 67/033* (2006.01)

(52) U.S. Cl. .............................. 435/325; 435/4; 800/3; 800/8

(58) Field of Classification Search ............... 536/23.1, 536/24.1; 424/93.1; 435/325, 455
See application file for complete search history.

(56) References Cited

U.S. PATENT DOCUMENTS 5,843,780 A * 12/1998 Thomson ..................... 435/363
6,245,564 B1 * 6/2001 Goldman et al. ........... 435/368
6,303,370 B1 * 10/2001 Kappen et al. .......... 435/320.1
6,528,245 B2 * 3/2003 Sanchez-Ramos et al. ... 435/1.1
6,566,089 B1 * 5/2003 Shan et al. .................... 435/29

FOREIGN PATENT DOCUMENTS

EP     483014      4/1992
WO     98/4688     2/1998

OTHER PUBLICATIONS

Moreadith, et al. (1997) J. Mol. Med., 75: 208-216.*
Pera, et al. (2000) J. Cell. Sci., 113: 5-10.*
Pan, et al. (2002) Cell Res., 12(5-6): 321-29.*
Dinsmore, et al. (1998) Theriogenology, 49: 145-51.*
Ling, et al. (1998) Exp. Neurol., 149(2): 411-23.*
Knight (1988) Proc. Natl. Acad. Sci., USA, 85: 3130-34.*
Bronson, et al. (1996) Proc. Natl. Acad. Sci., USA., 93: 9067-72.*
Patankar, et al. (1997) J. Neurosci., 17(11): 4076-86.*
Boundy, et al. (1998) J. Neurosci., 18(23): 9989-95.*
Sawamoto, K., Nakao, N., Kobayashi, K., Matsushita, N., Takahashi, H., Kakishita, K., Yamamoto, A., Yoshizaki, T., Terashima, T., Murakami, F., Itakura, T., and Okano, H. "Visualization, direct isolation, and transplantation of midbrain dopaminergic neutrons"; PNAS; May 22, 2001; vol. 98, No. 11; 6423-6428.

* cited by examiner

*Primary Examiner*—Joseph Woitach
*Assistant Examiner*—Robert M. Kelly
(74) *Attorney, Agent, or Firm*—Wenderoth, Lind & Ponack, L.L.P.

(57) ABSTRACT

The invention of this application provides a method comprising introducing a reporter nucleic acid molecule that expresses a fluorescent protein under control of the promoter/enhancer of a gene that is expressed in dopaminergic neurons, into each of cells, and isolating fluorescence-emitting cells. The invention also provides a method for visualizing and identifying dopaminergic neurons alive that exist with in cells, which comprises introducing the above-mentioned reporter nucleic acid molecule into each of cells, and measuring the fluorescence distribution within the cells. The invention further provides a method for identifying a dopaminergic neurons-inducing factor, which comprises introducing the reporter nucleic acid molecule into cells that have the ability to differentiate into dopaminergic neurons, then incubating the cells with a candidate substance, and determining whether the candidate substance is a dopaminergic neurons-inducing factor by using the fluorescence of the cells as an indicator.

20 Claims, 2 Drawing Sheets

METHOD OF CONCENTRATING AND SEPARATING DOPAMINERGIC NEURONS

This application is a 371 of PCT/JP00/08674 filed Dec. 7, 2000.

TECHNICAL FIELD

The invention of this application relates to a method for enrichment and/or isolation of dopaminergic neurons. More precisely, it relates to an efficient and reliable method of identifying dopaminergic neurons for enriching and/or isolating them, in which the dopaminergic neurons are useful as graft cell for treatment of Parkinson's disease and as materials for developing methods of treating the disease.

BACKGROUND ART

Parkinson's disease is caused by selective degeneration and deletion of dopaminergic neurons in mesencephalic substantia nigra. For treating it, the effectiveness of transplanting a fetal mesencephalon tissue that contains a large amount of dopaminergic neurons (or cells having the differentiation potency into dopaminergic neurons), into the brain (striate body) of patients has been verified.

In fact, however, it is impossible to secure plenty of fetal brain tissue for use in ordinary clinics. Therefore, donor cells substitutable for fetal mesencephalon are desired.

For example, it is under investigation to use cells that have been differentiated into dopaminergic neurons from a large number of undifferentiated neural cells, for donor cells for transplantation. In addition, it is also under investigation to use cells having been differentiated from non-neural cells such as ES cells or marrow mesenchymal cells into dopaminergic neurons, for donor cells for transplantation. These cells can be differentiated into the intended dopaminergic neurons, after in vitro expansion, and therefore could be a means for solving the problem of shortage of donors. Moreover, since marrow mesenchymal cells can be safely collected from adults, it is possible to prepare dopaminergic neurons for transplantation from the cells of patients themselves. Accordingly, if those kinds of therapeutic strategy become available, they will solve not only the problem of shortage of donors and the technical problem of rejection against grafts, but also the ethical problem involved in obtaining dopaminergic neurons from aborted babies.

However, the method for the efficient induction of dopaminergic neurons from undifferentiated cell groups is not as yet completely established. In addition, from undifferentiated cell groups, various cells other than dopaminergic neurons are differentiated. Further, there is a risk that undifferentiated cell groups may include cells that will form tumors after transplanted. Accordingly, if dopaminergic neurons that had been differentiated in vitro are intended to be used for transplantation, they must be selectively separated from many kinds of cell groups.

As so mentioned hereinabove, enriched dopaminergic neurons are expected to be useful for graft donor cells for treatment of Parkinson's disease, etc. In addition, the technique of enrichment and/or isolation of dopaminergic neurons is extremely useful for identifying novel proteins and genes that are expressed specifically in these neurons. This is because such proteins and genes are expected to lead to novel drugs for the treatment.

In addition, it is extremely important to identify the factor that induces the in vitro differentiation of dopaminergic neurons from undifferentiated cells. Not only the factor is useful for efficiently inducing dopaminergic neurons from undifferentiated cells, but also the factor itself is expected to lead to novel drugs for the treatment.

As yet, however, no method has been established for isolating dopaminergic neurons from in vivo tissues or from cells being cultured in vitro.

Needless-to-say, not only the method for searching for the factor of in-vitro induction of dopaminergic neurons but also the method necessary for the search, which is for visualizing living dopaminergic neurons, has not been established as yet.

One object of the invention of this application is to provide a method for visualizing living dopaminergic neurons in cells including various types of different cells, to thereby enrich and isolate the dopaminergic neurons to a high purity.

Another object of the invention of this application is to provide the dopaminergic neurons isolated by the method.

Still another object of the invention of this application is to provide a method for identifying a factor that induces the differentiation of dopaminergic neurons from undifferentiated cells.

DISCLOSURE OF THE INVENTION

In its first aspect, the invention of this application provides a method for enrichment and/or isolation of dopaminergic neurons from cells, which comprises introducing a reporter nucleic acid molecule that expresses a fluorescent protein under control of the promoter/enhancer of a gene that is expressed in dopaminergic neurons, into each of the cells, and isolating the fluorescence-emitting cells.

In its second aspect, the invention of this application provides cells under culture condition, which is enriched and isolated by the method of the first aspect of the invention.

In its third aspect, the invention of this application provides a method for identifying dopaminergic neurons alive, which comprises introducing a reporter nucleic acid molecule that expresses a fluorescent protein under control of the promoter/enhancer of a gene that is expressed in dopaminergic neurons, into each of the cells, and measuring the fluorescence distribution among these populations of the cells.

In its fourth aspect, the invention of this application provides a method for identifying a factor which induce the cells that have an ability to differentiate into dopaminergic neurons, into dopaminergic neurons, the method comprising introducing a reporter nucleic acid molecule that expresses a fluorescent protein under control of the promoter/enhancer of a gene that is expressed in dopaminergic neurons, into cells, incubating the cells with a candidate substance, and determining whether the candidate substance is the dopaminergic neurons-inducing factor by using the fluorescence of the cells as an indicator.

In the methods of the first and third aspects of the invention, the following are preferred embodiments:

the gene that is expressed in dopaminergic neurons is a tyrosine hydroxylase gene;

the fluorescent protein is a green fluorescent protein;

the cells are derived from brain;

the cells are ES cells;

the cells are derived from marrow mesenchymal cells;

the cells are derived from human;

each of the cells is introduced with a recombinant vector having the reporter nucleic acid molecule, and/or the cells are derived from an animal or its progeny which is obtained through the ontogenic development of non-human totipotent cell into which the reporter nucleic acid molecule is introduced.

In another preferred embodiment of the first aspect of the invention, the fluorescence-emitting cells are enriched and isolated by the use of a cell sorter.

Preferred embodiments of the fourth aspect of the invention are the following:

the gene that is expressed in dopaminergic neurons is a tyrosine hydroxylase gene;

the fluorescent protein is a green fluorescent protein;

the cells that have an ability to differentiate into dopaminergic neurons are derived from the brain;

the cells that have an ability to differentiate into dopaminergic neurons are ES cells;

the cells that have an ability to differentiate into dopaminergic neurons are marrow interstitial cells;

the cells that have an ability to differentiate into dopaminergic neurons are derived from human;

the cells that have an ability to differentiate into dopaminergic neurons are introduced with a recombinant vector having the reporter nucleic acid molecule; and/or the cells that have an ability to differentiate into dopaminergic neurons are derived from an animal or its progeny which is obtained through the ontogenic development of non-human totipotent cell into which the reporter nucleic acid molecule is introduced.

THE BEST MODE FOR CARRYING OUT THE INVENTION

Figure 1:
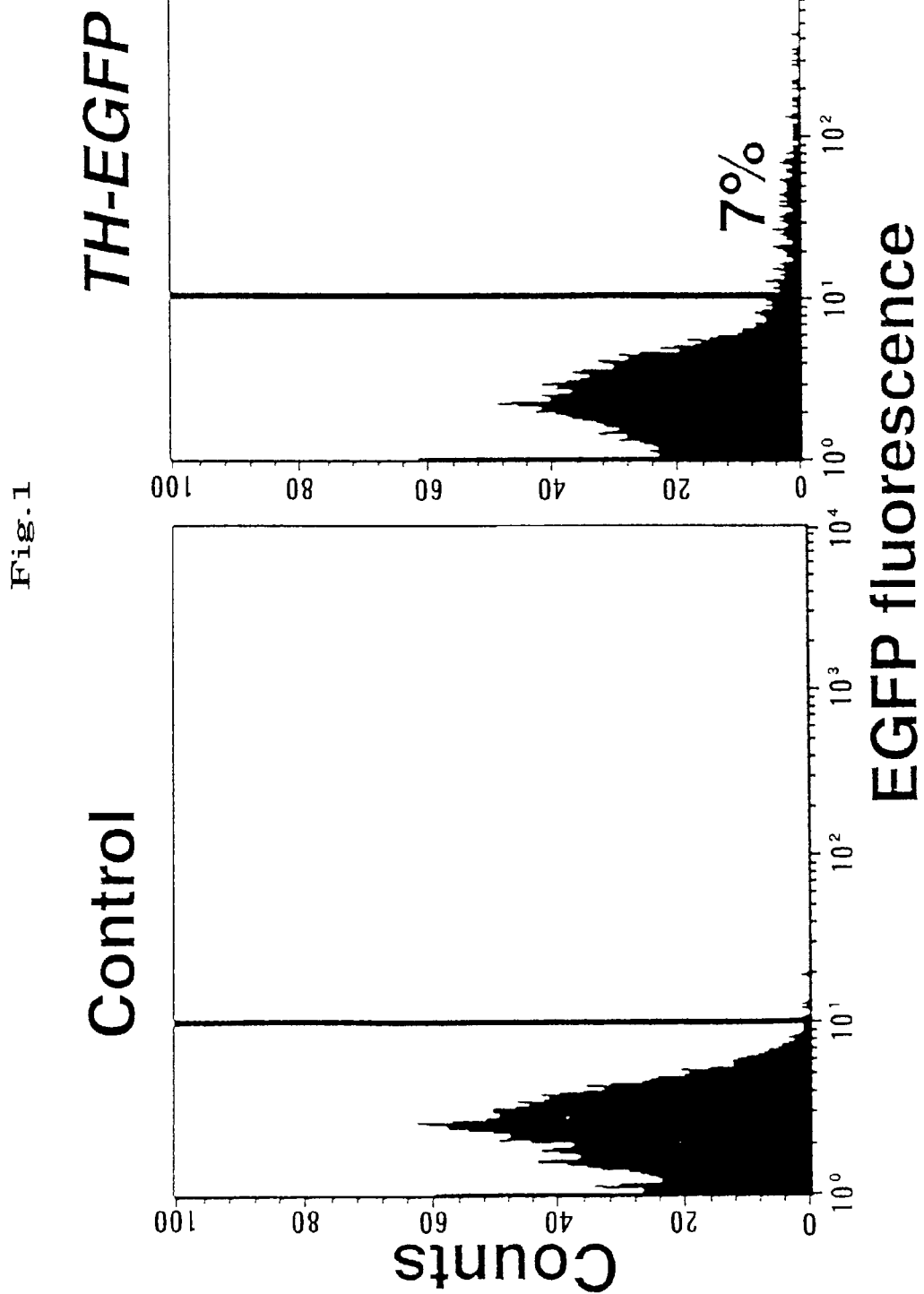
FIG. 1 shows the results of FACS analysis of dispersions of cells obtained from fetal, TH-EGFP transgenic mouse mesencephalon.

The first invention is a method that is characterized by the induction of a reporter nucleic acid molecule, which expresses a fluorescent protein under control of the promoter/enhancer of a gene that is expressed in dopaminergic neurons, into various type of animal-derived cell, and the isolation of the fluorescence-emitting cells from the cells.

The reporter nucleic acid molecule to be introduced into the cells is a fusion gene which consists of a DNA sequence encoding the promoter/enhancer of a gene that is expressed in dopaminergic neurons and a fluorescent protein-encoding DNA sequence in its downstream.

For the promoter/enhancer of the gene that is expressed in dopaminergic neurons, herein employable is the promoter sequence of a tyrosine hydroxylase (TH) gene of various kinds of animals, and especially preferred is the promoter of a rat TH gene. The rat TH gene promoter sequence was registered as GenBank Accession No. AF069036. For use herein, it may be obtained by screening the rat genome library, using a probe constructed on the basis of the known sequence; or it may be obtained through PCR using synthetic primers.

For the fluorescent protein, herein usable is any of scyphomedusa-derived green fluorescent protein or sea anemone-derived red fluorescent protein (RFP). Especially preferred are GFP and GFP derivatives (e.g., those described in Current Biology 6(2): 178-182, 1996). For the GFP-encoding polynucleotide, its cDNA is known (Gene 111(2): 229-233, 1990; GenBank No. M62654). Clones of EGFP cDNA (EGFP Poly(A), from Clontech) are also available.

For the cells into which such a reporter nucleic acid molecule is introduced, differentiated neural cells derived from brains of animals including human can be used. Also usable are dopaminergic neurons which are in-vitro differentiated and induced from neural stem cells, ES cells, marrow mesenchymal cells or the like having the differentiation potency into dopaminergic neurons. For inducing the undifferentiated cells of these types into dopaminergic neurons, employable are any known methods (for example, for neural stem cells, referred to is Nat. Neurosci., 1: 290-295, 1998; and for ES cells, referred to are Nat. Biotechnol., 18: 675-679, 2000, and Neuron 28: 31-40, 2000).

For introducing such a reporter nucleic acid molecule into cells, employable is a method of introducing an expression vector having the reporter nucleic acid molecule insert therein, into each cell culture. The expression vector may be a plasmid vector for expression in animal cells. For introducing such a plasmid vector into cells, employable is any of an electroporation method, a calcium phosphate method, a liposome method or a DEAE-dextran method. Also employable is a method of infecting cells with a viral vector such as an adenoviral vector.

In case where the method is directed to non-human animals, transgenic animals having the intended reporter nucleic acid molecule introduced thereinto may be produced, and their cells thus having the reporter nucleic acid molecule may be used herein. Such transgenic animals may be produced in any known methods (for example, as in Proc. Natl. Acad. Sci., USA 77, 7380-7384, 1980). The non-human transgenic animals have the reporter nucleic acid molecule in all their somatic cells. From them, therefore, the tissue in the central nervous system is taken out, and the cells that emit a fluorescent signal are isolated from it. In that manner, a large amount of the intended dopaminergic neurons can be obtained.

For enrichment and isolation of the dopaminergic neurons from the cells into which the intended reporter nucleic acid molecule has been introduced according to any of the methods mentioned above, the cells that emit the fluorescent signal may be separated one after another from the cultured cells by the use of a fluorescent microscope. However, for greatly increasing the work efficiency, it is preferable to use a cell sorter (e.g., fluorescence activated cell sorter: FACS). Using such a cell sorter, the intended dopaminergic neurons can be automatically enriched and isolated.

The method of the third aspect of the invention is for visualizing and identifying the dopaminergic neurons alive that exist within a mixed cell population. The method comprises introducing the above-mentioned reporter nucleic acid molecule into each of cells, and measuring the fluorescence distribution in the cells. In this, the materials and the methods of nucleic acid molecule introduction into cells may be basically the same as those in the first aspect of the invention. The cells into which the reporter nucleic acid molecule has been introduced are observed with a microscope, and the dopaminergic neurons therein can be visualized and identified by the fluorescence distribution within the cells.

The method of the fourth aspect of the invention is for identifying a dopaminergic neurons-inducing factor. This comprises introducing an intended reporter nucleic acid molecule into cells that have the potency to differentiate into dopaminergic neurons, incubating the cells with a candidate substance, and determining whether the candidate substance is a dopaminergic neurons-inducing factor by using the fluorescence of the cells as an indicator. In this, the cells that have the potency to differentiate into dopaminergic neurons may be any of neural stem cells, ES cells, marrow mesenchymal cells or the like. The same reporter nucleic acid molecule as in the first aspect of the invention mentioned above is introduced into these undifferentiated cells, and a candidate substance is added to the cell culture medium. Whether the candidate substance induces the undifferentiated cells into dopaminergic neurons can readily be confirmed in the same manner as in the second aspect of the invention mentioned above.

The invention of this application is described more in detail and more concretely with reference to the following Examples, which, however, are not intended to restrict the scope of the invention.

EXAMPLES

1. Preparation of Transgenic Mouse

Constructed was a vector (RTH-GFP) that expresses GFP under the control of the promoter sequence of a rat TH gene. Concretely, the upstream 10-kb promoter sequence of a rat TH gene that is known to be expressed specifically in dopaminergic neurons (Mol. Brain Res., 27: 281-289, 1994; Mol Cells, 7: 394-398, 1997), was introduced into the upstream of EGFP cDNA (from Clontech) to construct a recombinant vector. Next, the recombinant vector was cleaved to be linear, and this was injected into the pronucleus of a zygote derived from an F1 mouse of C57BL/6J mouse and DBA/2J mouse. The gene-introduced zygote was transplanted into the oviduct of a surrogate mother in an ordinary manner, in which it grew into an individual, TH-EGFP-transgenic mouse.

2. Preparation of Cell Dispersion

The male TH-EGFP mouse was mated with a wild-type mouse. From the 12-day fetus taken out of it, the ventral mesencephalon was taken out. This tissue was processed in a solution of trypsin/EDTA, and its cells were dispersed through pipetting. The cells were cultured for 24 hours, and then reacted with an anti-TH antibody and a Texas Red-labeled secondary antibody to analyze them. The result confirmed that about more than half of the GFP-positive antibodies are TH-positive dopaminergic neurons.

3. Enrichment and Isolation of Dopaminergic Neurons with Cell Sorter

Propidium iodide was added to the cell dispersion prepared in the above 2, and this was passed through a nylon mesh to remove the non-digested tissue debris from it. Then, this was analyzed with an FACS Vantage (from Vector Dickinson). As in FIG. 1 showing the result, 7% cells in the cell dispersion gave a fluorescent signal.

Figure 2:
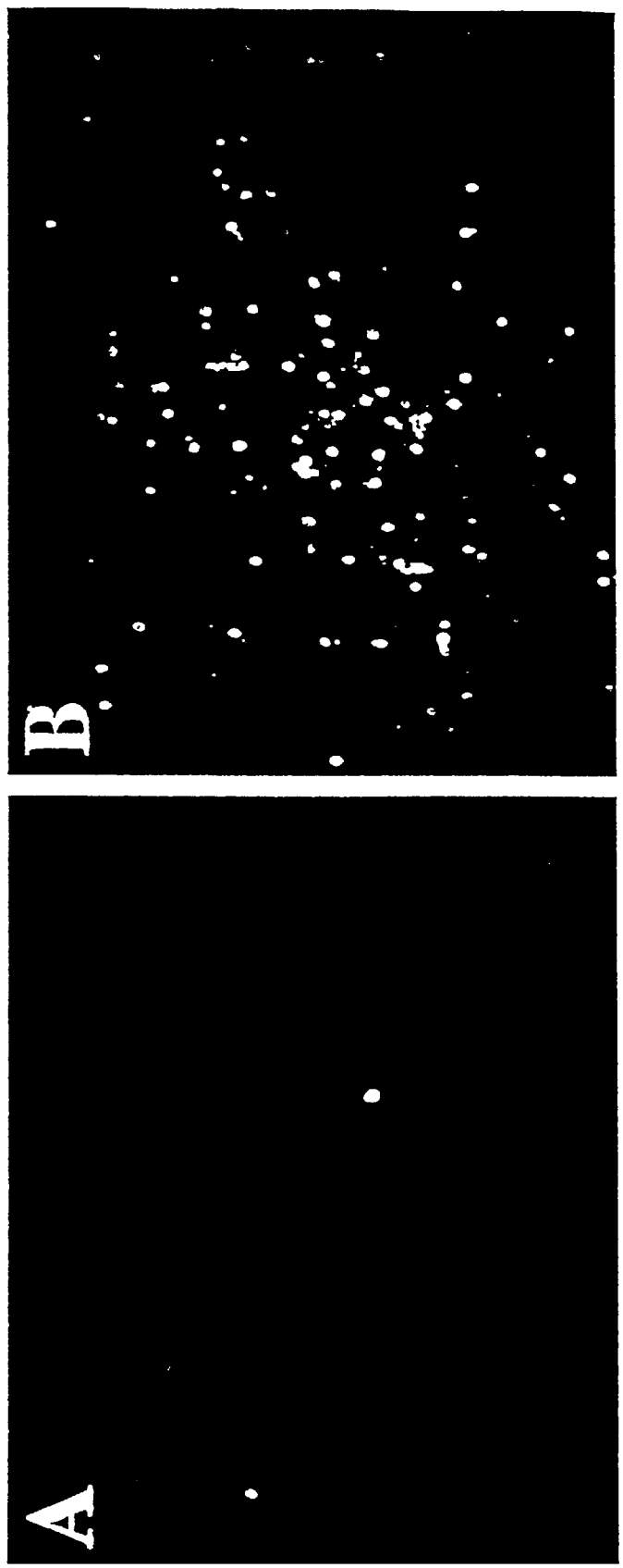
FIG. 2 shows the results of analysis of all cells (A) and FACS-sorted cells (B) in cell dispersions for GFP and TH gene expression.

Next, the propidium iodide-negative, GFP-emitting cells (living cells) were collected in a test tube. These were applied to a cover glass, and tested for the reactivity to the antibodies in the same manner as in the above 2. As in FIG. 2(B) showing the result, almost all the cells are positive to GFP and to TH. This means that the cells are dopaminergic neurons.

4. The cells obtained in the above 3 were transplanted in parkinsonism model rats with 6-OHDA administered thereto. After 5 weeks, the rats were checked for rotation behaviors to be caused by amphetamine administered thereto. For their disease symptoms, all the rats were significantly improved.

INDUSTRIAL APPLICABILITY

As described in detail hereinabove, the invention of this application provides a method for enrichment and/or isolation of dopaminergic neurons from cells consisting of different types of cells, and provides the dopaminergic neurons that are enriched to a high purity according to the method. The cells are useful not only for the material (cells for transplantation) for treatment of human Parkinson's disease, etc., but also for analyzing the causes and the symptoms of the disease and for developing the therapeutic techniques and the medicines for the disease. In addition, the invention of this application also provides a method for visualizing and identifying dopaminergic neurons alive, and provides, based on it, a method for identifying the factor that participates in induction of cells to differentiate into dopaminergic neurons. These methods make it possible to efficiently obtain graft cells for Parkinson's disease and others from undifferentiated cells. Further, the dopaminergic neurons-differentiating and inducing factor is useful for development of novel drugs for treatment.

The invention claimed is:

1. A method for enriching and/or isolating dopaminergic neurons from a non-human transgenic animal or its progeny, which comprises:
   introducing a recombinant vector comprising a reporter nucleic acid molecule that expresses a fluorescent protein under control of the promoter/enhancer of a tyrosine hydroxylase gene of the non-human animal into a fertilized egg of the non-human animal,
   developing the non-human fertilized egg whose genome comprises the reporter nucleic molecule into a non-human transgenic animal by transfer to a surrogate mother, and
   isolating cells that emit a fluorescent signal from a plurality of cells of the non-human transgenic animal or its progeny whose genome comprises the reporter nucleic acid molecule, wherein the fluorescence-emitting cells are dopaminergic neurons.

2. The method as claimed in claim 1, wherein the fluorescent protein is a green fluorescent protein.

3. The method as claimed in claim 1, wherein the plurality of cells are derived from brain of the non-human transgenic animal or its progeny.

4. The method as claimed in claim 1, wherein the plurality of cells are derived from marrow mesenchymal cells of the non-human transgenic animal or its progeny.

5. The method as claimed in claim 1, wherein the fluorescence-emitting cells are enriched and isolated by the use of a cell sorter.

6. A cell culture comprising cells that have been enriched and isolated by the method of claim 1.

7. A method for identifying live dopaminergic neurons from a non-human transgenic animal or its progeny, which comprises:
   introducing a recombinant vector comprising a reporter nucleic acid molecule that expresses a fluorescent protein under control of the promoter/enhancer of a tyrosine hydroxylase gene of the non-human animal into a fertilized egg of the non-human animal,
   developing the non-human fertilized egg whose genome comprises the reporter nucleic acid molecule into a non-human transgenic animal by transfer to a surrogate mother, and
   measuring the fluorescence distribution within a plurality of cells obtained from the non-human animal or its progeny whose genome comprises the reporter nucleic acid molecule, wherein the fluorescence is an indicator of live dopaminergic neurons.

8. The method as claimed in claim 7, wherein the fluorescent protein is a green fluorescent protein.

9. The method as claimed in claim 7, wherein the plurality of cells are derived from brain of the non-human transgenic animal or its progeny.

10. The method as claimed in claim 7, wherein the plurality of cells are derived from marrow mesenchymal cells of the non-human transgenic animal or its progeny.

11. A method for identifying a factor which induces cells to differentiate into dopaminergic neurons, which comprises:

introducing a recombinant vector comprising a reporter nucleic acid molecule that expresses a fluorescent protein under control of the promoter/enhancer of a tyrosine hydroxylase gene of the non-human animal into a fertilized egg of the non-human animal, developing the non-human fertilized egg whose genome comprises the reporter nucleic acid molecule into a non-human transgenic animal by transfer to a surrogate mother, incubating cells obtained from the non-human transgenic animal or its progeny whose genome comprises the reporter nucleic acid molecule with a candidate substance, and determining whether the candidate substance is the dopaminergic neuron-inducing factor by identifying cells that emit a fluorescent signal, greater than background fluorescence to indicate the presence of the dopaminergic neuron-inducing factor.

12. The method as claimed in claim 11, wherein the fluorescent protein is a green fluorescent protein.

13. The method as claimed in claim 11, wherein the cells that have an ability to differentiate into dopaminergic neurons are neural stem cells of the non-human transgenic animal or its progeny.

14. The method as claimed in claim 11, wherein the cells that have an ability to differentiate into dopaminergic neurons are marrow mesenchymal cells of the non-human transgenic animal or its progeny.

15. A method for enriching and/or isolating dopaminergic neurons from a transgenic mouse or its progeny, which comprises:

introducing a recombinant vector comprising a reporter nucleic acid molecule that expresses a fluorescent protein under control of the promoter/enhancer of a tyrosine hydroxylase gene of the mouse or the promoter/enhancer of a tyrosine hydroxylase gene obtained from a rat into mouse ES cells, developing the mouse ES cells whose genome comprises the reporter nucleic acid molecule into a transgenic mouse by introducing the ES cells into a blastocyst and transferring the blastocyst to a surrogate mother, and isolating cells that emit a fluorescent signal from a plurality of cells obtained from the transgenic mouse or its progeny whose genome comprises the reporter nucleic acid molecule, wherein the fluorescence-emitting cells are dopaminergic neurons.

16. The method as claimed in claim 15, wherein the fluorescent protein is a green fluorescent protein.

17. The method as claimed in claim 15, wherein the fluorescence-emitting cells are enriched and isolated by the use of a cell sorter.

18. A cell culture comprising the cells that have been enriched and isolated by the method of claim 15.

19. A method for identifying live dopaminergic neurons from a transgenic mouse or its progeny, which comprises:

introducing a recombinant vector comprising a reporter nucleic acid molecule that expresses a fluorescent protein under control of the promoter/enhancer of a tyrosine hydroxylase gene of the mouse or the promoter/enhancer of a tyrosine hydroxylase gene obtained from a rat into mouse ES cells, developing the mouse ES cells whose genome comprises the reporter nucleic acid molecule into a transgenic mouse by introducing the ES cells into a blastocyst and transferring the blastocyst to a surrogate mother, and measuring the fluorescence distribution within a plurality of cells obtained from the transgenic mouse or its progeny whose genome comprises the reporter nucleic acid molecule, wherein the fluorescence is an indicator of live dopaminergic neurons.

20. The method as claimed in claim 19, wherein the fluorescent protein is a green fluorescent protein.

* * * * *